US007125391B2

(12) United States Patent
Joze et al.

(10) Patent No.: US 7,125,391 B2
(45) Date of Patent: Oct. 24, 2006

(54) DEVICE WITH VACUUM BAG FOR PRESSURE THERAPY

(76) Inventors: Jeienc Joze, Prezrenje 18, 4244 Podnart (SI); Vogrin Sasa, Spodnja Volcina 86B, 2232 Spodnja Volcina (SI)

( * ) Notice: Subject to any disclaimer, the term of this patent is extended or adjusted under 35 U.S.C. 154(b) by 490 days.

(21) Appl. No.: 10/689,964

(22) Filed: Oct. 21, 2003

(65) Prior Publication Data

US 2004/0138596 A1 Jul. 15, 2004

(30) Foreign Application Priority Data

Oct. 21, 2002 (SI) ............................ P-200200258

(51) Int. Cl.
*A61F 5/37* (2006.01)
*A61F 5/01* (2006.01)

(52) U.S. Cl. .......................... 602/6; 128/869; 128/873; 128/878; 128/882

(58) Field of Classification Search .................... 602/6, 602/28, 29, 13; 128/DIG. 20; 601/6, 11, 601/152, 44
See application file for complete search history.

(56) References Cited

U.S. PATENT DOCUMENTS 3,745,998 A * 7/1973 Rose ............................ 602/6
3,762,404 A * 10/1973 Sakita ........................... 602/6
4,657,003 A * 4/1987 Wirtz ......................... 128/869
4,862,879 A * 9/1989 Coombs ...................... 602/13
5,121,756 A * 6/1992 Koledin ......................... 5/628
5,458,562 A 10/1995 Cooper ....................... 601/151
5,490,820 A * 2/1996 Schock et al. ................ 601/41
5,718,669 A * 2/1998 Marble .......................... 602/5
6,066,107 A * 5/2000 Habermeyer ................... 602/6
6,308,353 B1 10/2001 Van Steenburg ............... 5/632
6,918,393 B1 * 7/2005 Rugfelt et al. .............. 128/845
2003/0191437 A1 * 10/2003 Knighton et al. ........... 604/133
2006/0041206 A1 * 2/2006 Schaffrath et al. ............. 601/6

FOREIGN PATENT DOCUMENTS

DE 101 49 418 A1 4/2003

(Continued)

OTHER PUBLICATIONS

European Search Report dated Jul. 6, 2004.

*Primary Examiner*—Danton DeMille
(74) *Attorney, Agent, or Firm*—St. Onge Steward Johnston & Reens LLC

(57) ABSTRACT

The device with vacuum bag for pressure therapy solves the problem of accurate measuring of the under-pressure created in the vacuum bag and the problem of appropriate adjustment of the liner clothing to individual patients. he device with vacuum bag for pressure therapy according to the invention consists of a vacuum bag, specially designed liner clothing, and a control and measuring unit, situated in a housing, including a pressure gauge, which has direct connection to the vacuum bag through a tube. The air is sucked out from the bag through tubes attached on the one side to six connections on the vacuum bag and on the other side to connections provided on the housing. The liner clothing consists of several pieces designed for different parts of the body. The liner clothing pieces are made of two layers of porous fabric sewn together with longitudinal seams. The pockets made in this way are filled with granulated material, which enables close fitting of the liner clothing to the body, when the under-pressure is created in the vacuum bag, as the air between the particles is sucked out, too. The liner clothing pieces are bound together by means of VELCRO® brand fasteners.

6 Claims, 6 Drawing Sheets

FOREIGN PATENT DOCUMENTS

Figure 1:
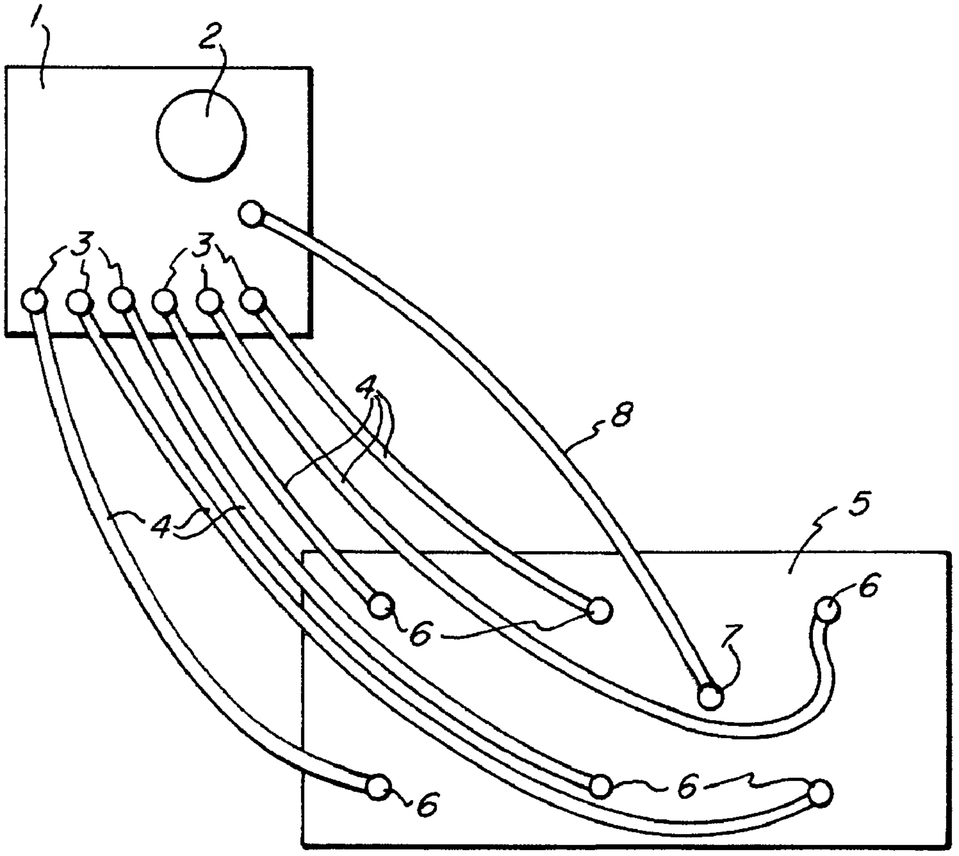

| | | | |
|---|---|---|---|
| FR | 2624008 | A1 * | 6/1989 |
| NL | 7016838 | | 5/1972 |
| SL | 9700234 | A | 4/1999 |

* cited by examiner

DEVICE WITH VACUUM BAG FOR PRESSURE THERAPY

This application claims priority of pending Slovenian Patent Application No. P-200200258 filed on Oct. 21, 2002.

FIELD OF THE INVENTION

The invention relates to a vacuum therapy device, particularly to a device for massage treatment and lymphatic drainage treatment of different stages of cellulitis as well as for treatment of scars and sports injuries.

BACKGROUND TO THE DISCLOSURE

The technical problem solved by the device, which is the subject of the present invention is a design and construction of accurate measuring of the under-pressure in the vacuum bag and a design and construction of special liner clothing for the user of the device. The accuracy of the measurement of the current value of the under-pressure in the vacuum bag depends on the position and distance of the pressure gauge. To ensure appropriate accuracy the pressure gauge should measure the under-pressure directly, therefore a direct physical link should be establish between the interior of the bag and the measuring instrument. The liner clothing to be put on by the patient before he/she puts on the vacuum bag should fit close to the body in order to create equal treatment conditions within the entire vacuum bag. Due to various body contours it is hard to achieve consistency of under-pressure in known devices as rigid felt is used as a liner. Consequently, all body parts in the bag cannot be treated under identical conditions. The technical problem to be solved is, therefore, how to achieve even conditions within the entire vacuum bag although the liner clothing is equal for all users, i.e. for small, tall, thin and fat patients. It is clear that the liner clothing should be flexible enough to fit well to different body shapes.

STATE OF THE ART OF ENGINEERING

Vacuum therapy has been used in various ways for treatment of different diseases for a long time. As far as massaging techniques are concerned, beside the suction cup therapy also the treatment of the entire body or larger parts of the body in a vacuum bag is used. The later is applied predominantly for treatment of blood circulation problems, for improvement of oxygenation in the organism, for detoxification of organism, for treatment of other conditions caused by lack of oxygen in the skin and/or in the subcutaneous tissue, and for treatment of weakened function of veins, for example for treatment of vasoconstriction and vasodilatation.

A massaging device using a vacuum bag has been for example designed by the Iskra Medical Company. In this device the liner clothing is made of felt, which is rather rigid, so the vacuum bag does not fit evenly tight causing different therapy conditions on different spots. Besides, the boots do not allow adaptation to feet of different sizes, which also reduces the adjustment possibilities for individual patients. Yet another drawback of the device concerns the solution of how the under-pressure in the bag is measured. Namely, the under-pressure is not measured directly within the vacuum bag causing inaccuracy in measured values.

Another device for pressure therapy and massage is described in the Slovene patent No. 9700234. The device enables either the under-pressure massage or the overpressure massage. To a control unit one or several massage units can be attached each massage unit being controlled separately. Twenty-eight control programs are presented producing different favorable and stimulation effects. The treatment unit is made of impermeable material that fits tight to the skin at least on its edges to form a close space between the unit and the skin. By sucking the air out from this close space the under-pressure is created. The treatment unit is not described; it is only presented in a drawing showing one-piece leg-bandage. During therapy the patient is wearing porous clothing, which is not described in detail. The therapy is conducted on a flexible table, which can be equipped with different accessories. Although the device enables a variety of therapies it is rather expensive due to a complex table. Insufficient adaptation of the therapy unit to individual patient is yet another problem. The therapy unit includes a probe for measuring the pressure; details on this solution are not presented.

DESCRIPTION OF THE INVENTION

The essential feature of the device with vacuum bag for pressure therapy according to the invention is a solution of efficient control of under-pressure by providing several connections for suction tubes on the vacuum bag and by providing direct, more accurate measurement of the under-pressure in the vacuum bag through a measuring tube. Further distinctive feature of the device is a design of special liner clothing that enables appropriate adjustment to different body shapes as it consists of several pieces for individual parts of the body, the pieces being flexible both in longitudinal and in transverse direction and being bound together by means of Velcro® brand fasteners to form a comfortable clothing for the patient.

The device with vacuum bag for pressure therapy is explained in detail by means of the following drawings showing:

FIG. 1—a schematic diagram of device with vacuum bag for pressure therapy

Figure 2:
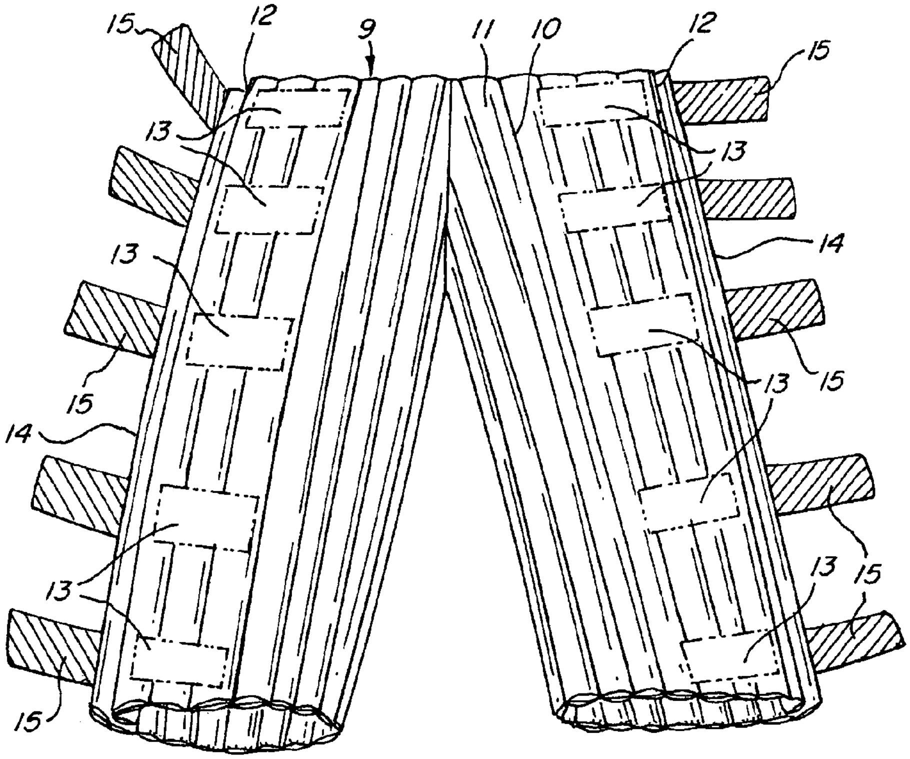

FIG. 2—liner trousers

Figure 3:
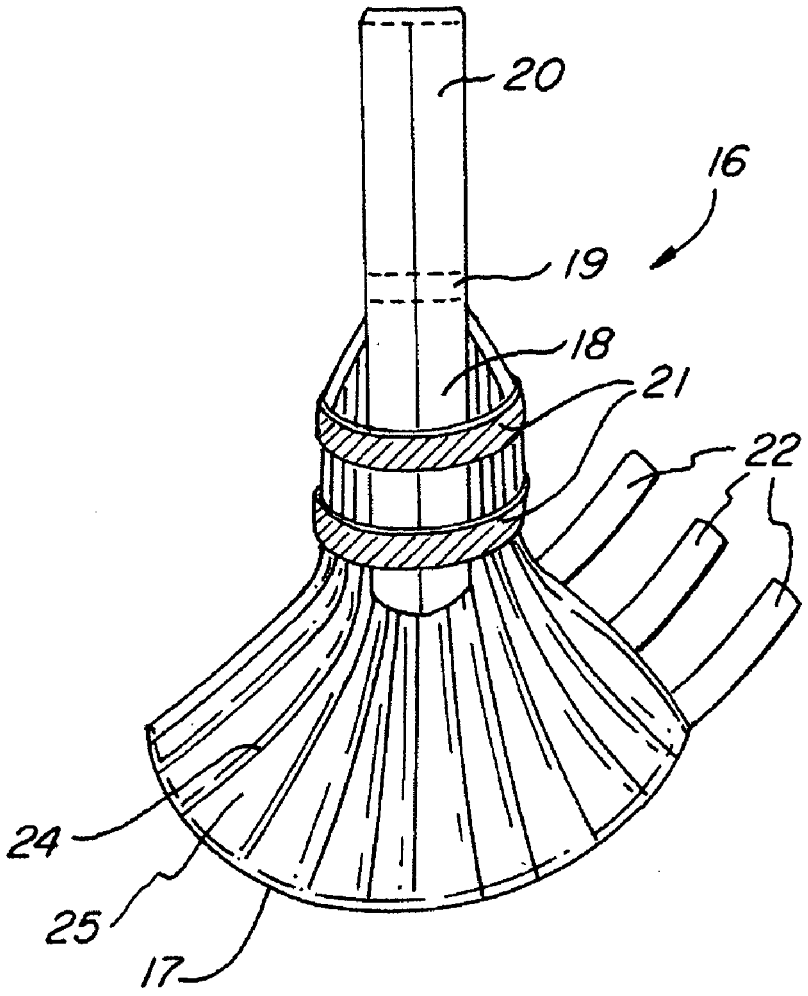

FIG. 3—open liner slipper

Figure 4:
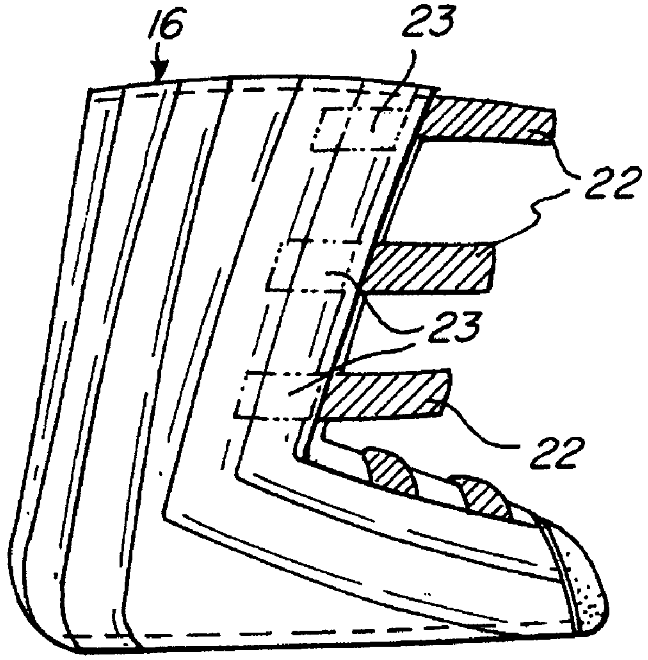
Figure 5:
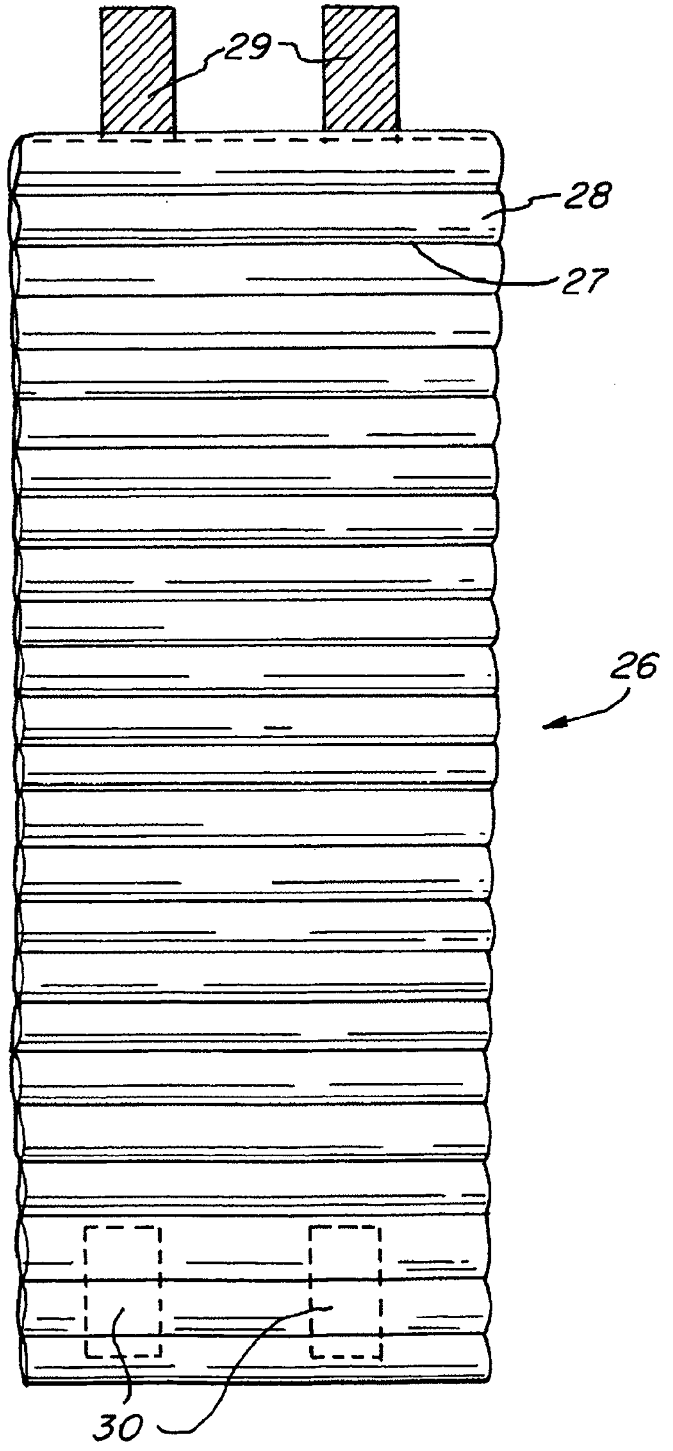

FIG. 4—liner slipper

FIG. 5—liner belt

Figure 6:
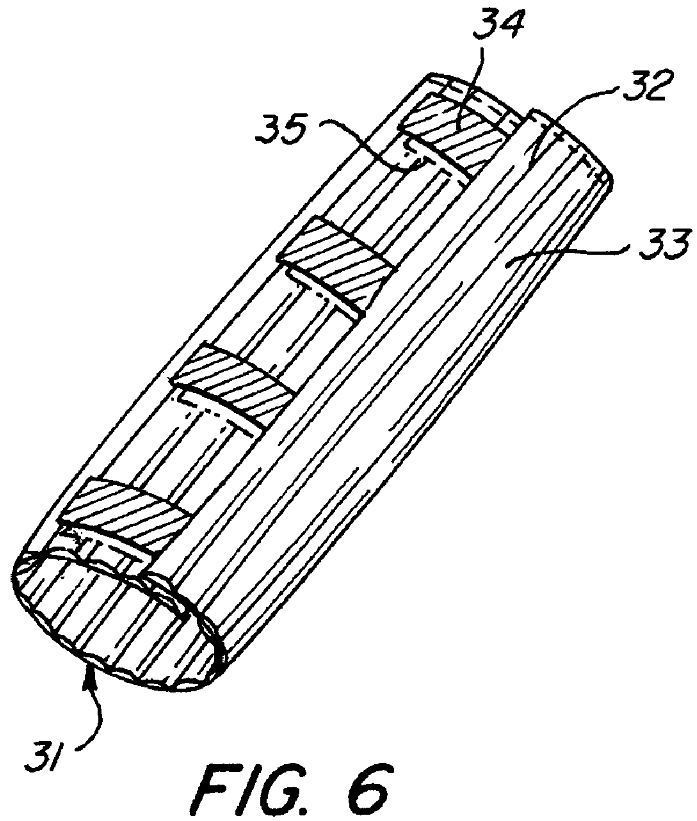

FIG. 6—liner sleeve

The device with vacuum bag for pressure therapy according to the invention comprises a vacuum bag 5 and special liner clothing, and a control and measuring unit, situated in a housing 1. The control and measuring unit includes a pressure gauge 2, which is linked directly to the interior of the vacuum bag 5 by means of a measuring tube 8. The measuring tube 8 is fastened to the bag 5 through the measuring connection 7. The suction tubes 4 are fastened to the control and measuring unit through connections 3 and to the vacuum bag 5 through six evenly arranged connections 6.

The liner clothing consists of several pieces designed for different parts of the body. The pieces are made of two layers of fabric sewn together with longitudinal seams. The pockets made in this way are filled with minute granulated material. The size and shape of the pockets depend on the size and form of the piece. When the air is sucked out of the vacuum bag 5, the granulated material fits tight to the body because the air between the particles is sucked out, too. The liner clothing pieces are bound together by means of VELCRO® brand fasteners.

The two layers of fabric of the liner trousers 9 are sewn together in longitudinal direction with seams 10 arranged in a distance between 3 cm to 10 cm. The pockets 11 made in this way are filled with granulated material. On the outer edge 12 of the front side of the liner trousers 9, six loop fastening tapes 13 are sewn, and on the outer edge 14 of the rear side of the liner trousers 9 six hook fastening tapes 15 are sewn, the six hook fastening tapes 15 being positioned at the same height as the six loop fastening tapes 13.

The liner slipper 16 consists of a fan-shaped part 17, a sole 18, a bend 19 and a tongue 20. The two layers of fabric of the part 17 are sewn together with seams 24 to form several trapezoidal pockets 25, which are filled with granulated material. In similar way the sole 18, the bend 19 and the tongue 20 are sewn with seams and the pockets made in this way are filled with granulated material. The part 17 has three hook fastening tapes 22 sewn on one edge and three loop fastening tapes 23 sewn on the other edge. The patient sets his/her foot on the sole 18, bends the tongue 20 to cover his/her instep, and fastens the fan-shaped part 17 around his/her ankle by means of fastening tapes 22 and 23. In this way the liner slipper is adapted to the size of the patient's foot.

The two layers of fabric of the liner belt 26 are sewn together with seams 27 that form the pockets 28 filled with granulated material. The liner belt 26 has two hook fastening tapes 29 sewn on one end and two loop fastening tapes 30 sewn on the other end.

The two layers of fabric of the liner sleeve 31 are sewn together with seams 32 that form the pockets 33 filled with granulated material. The liner sleeve 31 has four hook fastening tapes 34 sewn on one side and four loop fastening tapes 35 sewn on the other side.

The device with vacuum bag for pressure therapy according to the invention is characterized in that the measurement of the under-pressure is conducted directly by means of a measuring tube 8 fastened to a measuring connection 7 on the bag, hence, the under-pressure is measured in the bag itself and not in the measuring chamber, which is the case in known solutions. The liner clothing enables continuous sucking of the air out of the vacuum bag all around the treated body parts. As a result, the treatment is not painful, as there are no uncovered body parts, in which pain could occur due to pulling during suction of the air. Owing to granulated filler, the liner clothing fits very well to the shapes of the body when the air is sucked out from the bag 5, as also the air between the granules is sucked out and the granules are therefore arranged optimally within the pockets. Thus, the device according to the present invention instigates the most favorable effects of the vacuum therapy owing to accurate dosage of the under-pressure in the vacuum bag for individual patients and owing to close fitting of the liner clothing.

What is claimed is:

1. A device with vacuum bag for pressure therapy, comprising of a vacuum bag, a control and measuring unit, a housing, and special liner clothing, characterized in that a control and measuring unit is equipped with a pressure gauge and with vacuum pump connections, to which suction tubes for sucking the air from the bag are attached; that the bag has six evenly arranged connections for the suction tubes and a measuring connection for a measuring tube, which links the interior of the bag with the pressure gauge, so that the under-pressure is measured directly in the bag; that special liner clothing is provided for the user, the liner clothing comprising several pieces designed for different parts of the body and that the said clothing pieces are made of two layers of fabric sewn together with longitudinal seams to form pockets, filled with granulated material; that the granulated material fits tight to the body because also the air between the granules is sucked out, when the air is sucked out of the vacuum bag; that the liner clothing pieces are bound together by means of hook and loop fasteners.

2. A device of claim 1, wherein the special liner clothing includes liner trousers made of two layers of fabric sewn together in longitudinal direction with seams, the seams being arranged in a distance between 3 cm to 10 cm to form the pockets filled with granulated material, the liner trousers having six loop fastening tapes sewn on the outer edge of the front side and six hook fastening tapes sewn on the outer edge of the rear side, the six hook fastening tapes being positioned at the same height as the six loop fastening tapes.

3. A device of claim 1, wherein the special liner clothing includes a liner slipper comprising a fan-shaped part, a sole, a bend, and a tongue, the part being made of two layers of fabric sewn together with seams to form several trapezoidal pockets (25) filled with granulated material, and wherein also the sole, the bend and the tongue are made of two layers of fabric sewn together with seams to form the pockets filled with granulated material, the part having three hook fastening tapes sewn on one edge, and three loop fastening tapes sewn on the other edge, and wherein the liner sleeper is put on in such a manner that the foot is set on the sole, then the tongue is bended to cover the patient's instep and the fan-shaped part is fastened around the patient's ankle by means of fastening tapes.

4. A device of claim 1, wherein the special liner clothing includes a liner belt made of two layers of fabric sewn together with seams to form the pockets filled with granulated material, the liner belt having two hook fastening tapes sewn on one end and two loop fastening tapes sewn on the other end.

5. A device of claim 1, wherein the special liner clothing includes a liner sleeve made of two layers of fabric sewn together with seams to form the pockets filled with granulated material, the liner sleeve having four hook fastening tapes sewn on one side and four loop fastening tapes sewn on the other side.

6. A device according to claim 1, wherein the width of the pockets of the liner clothing is between 3 cm and 10 cm.

* * * * *

UNITED STATES PATENT AND TRADEMARK OFFICE

CERTIFICATE OF CORRECTION

PATENT NO. : 7,125,391 B2
APPLICATION NO. : 10/689964
DATED : October 24, 2006
INVENTOR(S) : Jelenc Joze et al.

It is certified that error appears in the above-identified patent and that said Letters Patent is hereby corrected as shown below:

Title Page

(76) Inventors: should read -- Jelene Joze, Prezrenje 18, 4244 Podnart (SI); Vogrin Sasa, Spodnja Volcina 86B, 2232 Spodnja Volcina (SI) --

Signed and Sealed this

Ninth Day of January, 2007

JON W. DUDAS
*Director of the United States Patent and Trademark Office*